United States Patent
Hirosawa

(10) Patent No.: US 6,348,966 B1
(45) Date of Patent: *Feb. 19, 2002

(54) MEASURING METHOD OF LIQUID CRYSTAL PRETILT ANGLE AND MEASURING EQUIPMENT OF LIQUID CRYSTAL PRETILT ANGLE

(75) Inventor: Ichiro Hirosawa, Tokyo (JP)

(73) Assignee: NEC Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/201,822

(22) Filed: Dec. 1, 1998

(30) Foreign Application Priority Data

Dec. 2, 1997 (JP) ................................ 9-331717

(51) Int. Cl.$^7$ .................................................. G01J 4/00
(52) U.S. Cl. ...................................... 356/364; 250/225
(58) Field of Search ................................ 356/364, 365, 356/366, 367; 359/93, 94; 250/225

(56) References Cited

U.S. PATENT DOCUMENTS

| 5,486,708 A | * | 1/1996 | Takahashi et al. |
| 5,822,263 A | * | 10/1998 | Campbell et al. |
| 5,903,352 A | * | 5/1999 | Ohsaki et al. ............... 356/364 |
| 5,973,817 A | * | 10/1999 | Robinson et al. |

FOREIGN PATENT DOCUMENTS

| JP | 1-162134 | 6/1989 |
| JP | 8-94444 | 4/1996 |
| JP | 8-094445 | 4/1996 |
| JP | 8-201227 | 8/1996 |
| JP | 8-201276 | 8/1996 |
| JP | 9-96815 | 4/1997 |
| JP | 9-243510 | 9/1997 |

* cited by examiner

Primary Examiner—Frank G. Font
Assistant Examiner—Tu T. Nguyen
(74) Attorney, Agent, or Firm—Sughrue Mion, PLLC

(57) ABSTRACT

A linearly polarized light is condensed by a lens 4 and set incident on a liquid crystal sample 5 with the incident angle being distributed continuously. The incident angle dependence of the polarization of the transmitted light is measured by a method of rotating an analyzer and the like, and thereby a pretilt angle of the liquid crystal sample is determined.

13 Claims, 13 Drawing Sheets

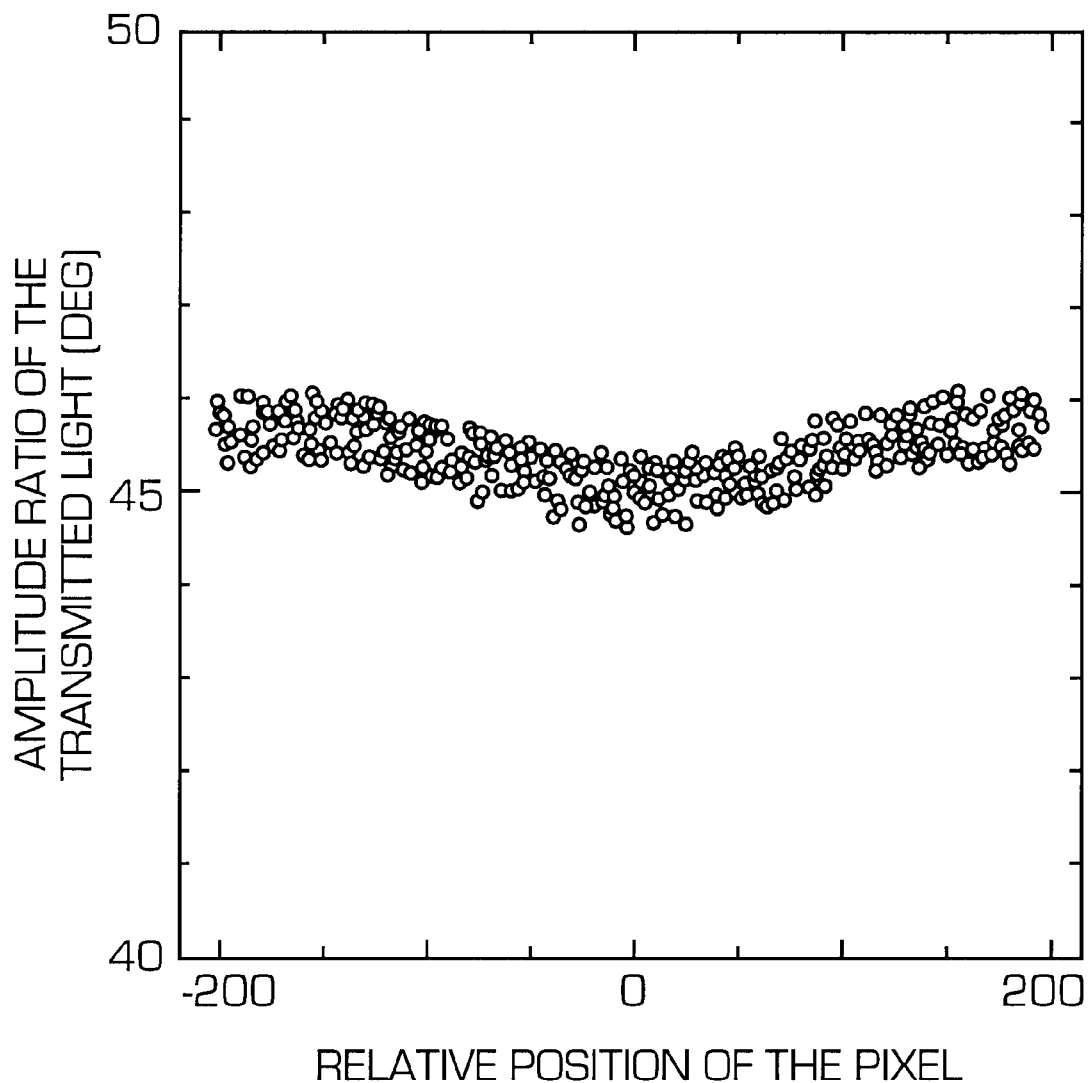

MEASURING METHOD OF LIQUID CRYSTAL PRETILT ANGLE AND MEASURING EQUIPMENT OF LIQUID CRYSTAL PRETILT ANGLE

BACKGROUND OF THE INVENTION

1. Field of the Invention

The present invention relates to an estimation method for a film having the optical anisotropy due to the alignment of molecules, for example, a liquid crystal alignment layer and the like which provides the initial orientation to the liquid crystal molecules in a liquid crystal display device.

2. Description of the Related Art

The crystal rotation method ( described by T. J. Scheffer and J. Nehring in Journal of Applied Physics, Vol. 48, pp.1783, 1977) has been widely employed as an optical method of measuring an angle that liquid crystal molecules in an antiparallel cell make with the reverse of a substrate. In this method, with the linearly polarized light incident on the sample, the optical retardation(phase shift) of the transmitted light which is generated through birefringence is measured as a function of the incident angle. On the other hand, instead of the direct measurement of the dependence of the polarization in the transmitted light on the incident direction, another measuring method in which an analyzer is placed behind a sample and the quantity of light transmitted through the analyzer is monitored as a function of the incident angle is also widely utilized.

However, the above-mentioned conventional techniques have the following problems as pointed out, for example, by K.-Y. Han et al. in Japanese Journal of Applied Physics, Vol. 32, pp. L1242–1244,L277–279 1993.

That is, because the liquid crystal is held between a pair of glass substrates, the refraction at the substrate causes a shift in the incident position of the light on the liquid crystal section, as the incident angle is changed. As the place through which the light passes within the liquid crystal is varied, the polarization of the transmitted light directly reflects the variance in thickness of the liquid crystal layer with the place, which hinders the accurate measurements. The incident angle of the light on the sample is usually changed by rotating the sample so that the relative position between the incident light and the transmitted light also changes, accompanying with the sample rotation. As a result, in order to carry out an accurate polarization measurement of the transmitted light, it is necessary for the positions of an analyzer and the like to be adjusted according to the thickness, the material and the rotation angle of the sample and the measuring efficiency of this method becomes low.

SUMMARY OF THE INVENTION

A primary object of the present invention is to provide a method of determining a pretilt angle of liquid crystal molecules with high accuracy, by measuring the incident angle dependence of the polarization of the transmitted light, wherein, instead of controlling the incident angle of the light through the sample rotation, the incident light is first condensed by a lens and the light incident on a sample is made to contain components with a plurality of incident angles, simultaneously.

Accordingly, in light of above problems, an object specified by the present invention is to provide a method of measuring a liquid crystal pretilt angle which determines a liquid crystal pretilt angle by setting the incident light with a given polarization on a liquid crystal sample and measuring the polarization of the transmitted light; wherein:

being condensed by a lens, said incident light with a given polarization is turned to have the incident angle of being distributed continuously and set incident on said liquid crystal sample; and the dependence of the polarization of said transmitted light on the incident angle is measured and thereby a pretilt angle of said liquid crystal sample is determined.

Another object of the present invention is to provide a method of measuring a liquid crystal pretilt angle which determines a liquid crystal pretilt angle by setting the incident light with a given polarization on a liquid crystal sample and measuring the polarization of the transmitted light;

wherein:

said liquid crystal sample comprises a liquid crystal material, transparent substrates sandwiching that liquid crystal material and hemispherical prisms which are placed on both of outer sides of the transparent substrates and have approximately the same refractive index as that of those transparent substrates; and by means of hemispherical prisms, said incident light with a given polarization is turned to have the incident angle of being distributed continuously and set incident on said liquid crystal sample; and the dependence of the polarization of said transmitted light on the incident angle is measured and thereby a pretilt angle of said liquid crystal sample is determined.

In the method of measuring a liquid crystal pretilt angle in accordance with the present invention, as mentioned above, the use of a lens or hemispherical prisms enables turning of the polarized light to have the incident angle of being distributed continuously and set incident on a liquid crystal sample without rotating the sample. Therefore, the deterioration in accuracy, resulting from non-uniformity of the sample, does not occur and a pretilt angle of the liquid crystal can be measured with accuracy as well as high speed.

Another object of the present invention is to provide an equipment of measuring a liquid crystal pretilt angle; comprising:

a light source;

a polarizer which polarizes the emitted light from that light source;

a holder which holds a liquid crystal sample as an object of the measurement;

lenses placed before and behind that holder;

a means for measuring, with the light having passed through said liquid crystal sample, the amplitude ratio of said transmitted light and/or the optical retardation of said transmitted light; and a means for determining a liquid crystal pretilt angle from said measured polarization.

An equipment of measuring a liquid crystal pretilt angle according to the present invention, has such an arrangement as described above that can carry out the above-mentioned method of measuring a liquid crystal pretilt angle favourably.

In the present invention, a lens or hemispherical prisms are utilized in incidence of the polarized light on the liquid crystal sample so that it is possible to set the incident light in a state where the incident angle is distributed continuously, without rotating the sample. Therefore, a deterioration in accuracy, resulting from non-uniformity of the sample, does not occur and a pretilt angle of the liquid crystal can be measured with accuracy as well as high speed.

BRIEF DESCRIPTION OF THE DRAWINGS

FIG. 13 is a plot showing the relationship between the amplitude ratio of the transmitted light and the relative position of the pixel.

DETAILED DESCRIPTION OF THE PREFERRED EMBODIMENTS

Figure 1:
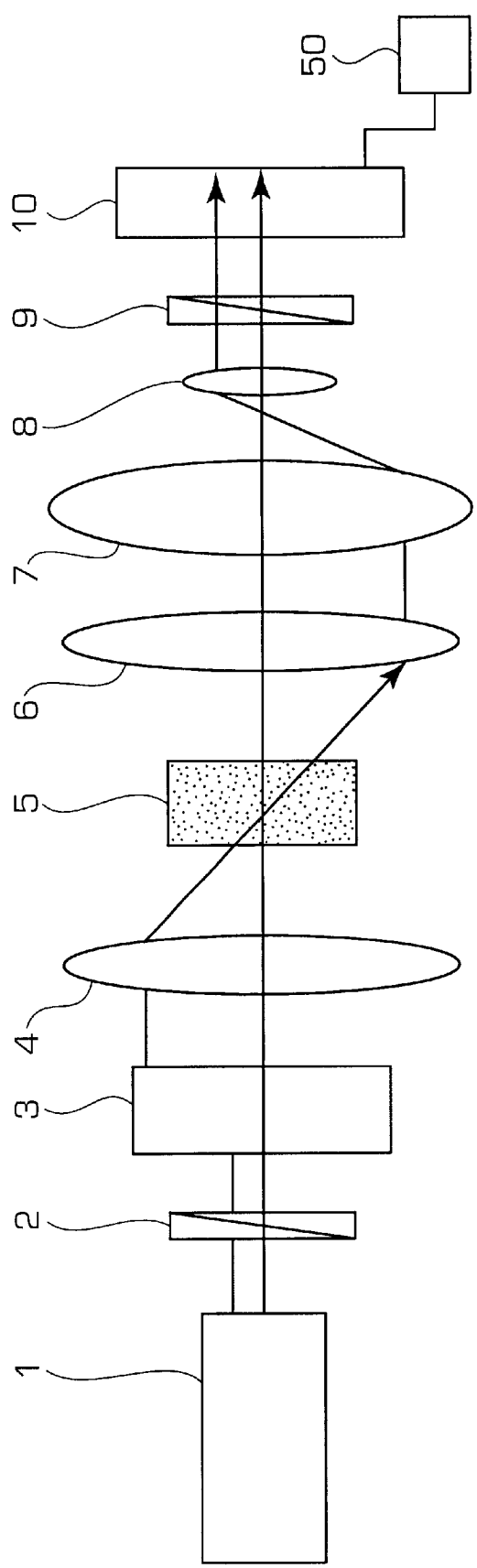
FIG. 1 is a schematic diagram illustrating an example of an equipment of measuring a liquid crystal pretilt angle in accordance with the present invention.

In the present invention, the polarized light incident on a liquid crystal sample may be either circularly polarized or linearly polarized. Further, the incident light on the liquid crystal sample is usually monochromatic and with a given polarization.

In the case of a linear polarization, the direction of polarization for the linearly polarized light is set to make, favourably, an angle of 42~48 degree, and more favourably an angle of 44~46 degree, with the azimuthal orientation of the liquid crystal molecules within plane. The most favourable angle is 45 degree. At such an angle, the optical retardation of birefringence arisen in the transmitted light becomes the maximum.

When the incident light is polarized circularly using a polarizer and a ¼-wave plate and the polarization of the transmitted light is measured in all directions as a function of the incident angle by a two-dimensional detector, no restriction exists with respect to the orientation of liquid crystal molecules in the sample unlike in the case where the incident light is linearly polarized. This enables a rapid measurement even for a sample with an unknown liquid crystal orientation.

In the present invention, a liquid crystal sample refers to a liquid crystal material sealed in a cell and, for example, a sample in which a liquid crystal material is sandwiched by a pair of transparent substrates is utilized.

Further, in the present invention, said incident angle dependence of said transmitted light can be measured by either the analyzer rotation method or the phaser rotation method. The analyzer rotation method is a method of analyzing the polarization of the light by making the light transmit to an analyzer which is set at certain given azimuths, and thereupon measuring the intensity of the transmitted light. Measured at more azimuthal points, the accuracy in the measurement improves. Meanwhile the phaser rotation method is a method wherein the quantity of the transmitted light is first expressed as a function of the azimuth of a ¼-wave plate, for which the ratio of the amplitude reflectance is obtained and then the optical retardation and the amplitude ratio are determined. For example, a ¼-wave plate is placed in immediate front of an analyzer and, by rotating the ¼-wave plate within plane, the dependence of the output intensity of the transmitted light on the azimuth of the ¼-wave plate is measured and thereby the polarization of the transmitted light is obtained.

Between the above methods of measuring the incident angle dependence, the phaser rotation method is more favourable. Compared with the analyzer rotation method, this phaser rotation method can carry out the measurement of the optical retardation component of the transmitted light, including the zone recognition, very rapidly.

In the present invention, the light passed through the sample is changed into a parallel beam by a lens and passes through both of a ¼-wave plate and an analyzer or only through an analyzer, and thereafter the intensity is measured by a one-dimensional or two-dimensional detector.

Further, when the thickness of a liquid crystal layer of the sample is equal to or more than 15 $\mu$m, the optical retardation of birefringence arisen in the transmitted light is large so that the incident angle dependence of the optical retardation of birefringence can be obtained by measuring the quantity of light transmitting the analyzer.

EXAMPLE 1

Referring to the drawings, the embodiments of the present invention are described below.

FIG. 1 is a schematic diagram illustrating an example of an equipment of measuring a liquid crystal pretilt angle in accordance with the present invention. Setting the linearly polarized light incident on a liquid crystal sample, a liquid crystal pretilt angle is measured through monitoring the quantity of light that is transmitting a polarizer. The light emitted from a light source 1 passes through a polarizer 2 and, being linearly polarized, is expanded by a beam expander 3. As a light source, a 1 mW He-Ne laser is used and the beam expander turns the light into a parallel beam with a diameter of approximately 25 mm. The light is then condensed by a lens 4 and set incident on a liquid crystal sample which is placed at a focal position of the lens. For this condenser, a combination lens with an aperture of 60 mm and a focal distance of 20 mm is used. The light passed through a sample 5 is returned into a parallel beam by a lens 6 having the same norm as the lens 4 and then changed into a parallel beam with a diameter of 3 mm by lenses 7 and 8. After this light passes through an analyzer 9, it goes into a detector 10. As a detector 10, a two-dimensional cooling-type image intensifier (512×512) manufactured by Hamamatsu Photonics is employed.

With this set-up, two liquid crystal samples were measured as follows. Glass substrates 7059 from Corning Inc. with a thickness of 1.1 mm were spin-coated with an alignment material PI-A produced by Nissan Chemical Industries Ltd.. After baked at 250° C. for 1 hour, the surface was rubbed with the rayon cloth. A cell was then assembled by sticking a pair of glass substrates together with adhesive in such a way that the rubbing directions thereof were opposite to each other. In this, there were prepared two cells, a cell A made using the adhesive mixed with a 6 $\mu$m spacer and a cell B made with the adhesive with a 20 $\mu$m spacer. These cells were filled, through a capillary action, with the nematic liquid crystal produced by Merck Ltd. under the trade name of ZNI-2293.

Figure 2:
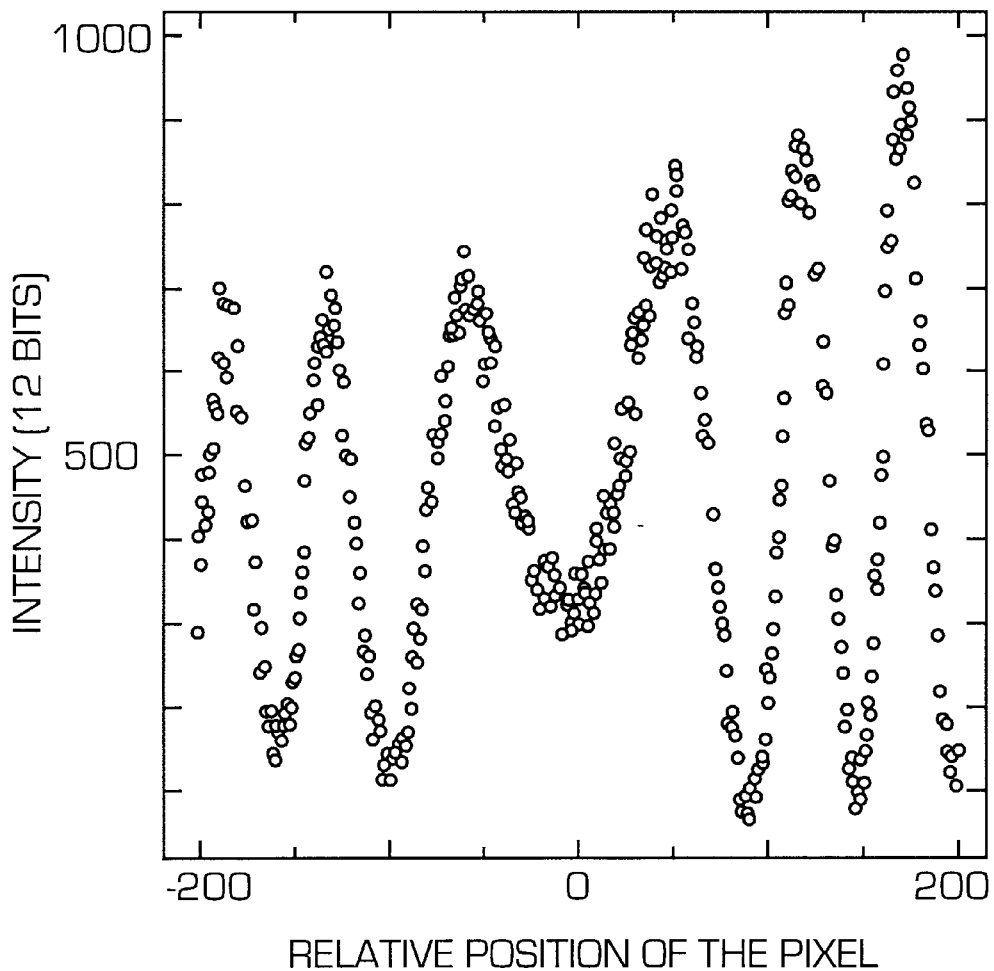
FIG. 2 is a plot showing the polarization of the liquid crystal sample A which is measured in the measuring equipment of a liquid crystal pretilt angle of FIG. 1 by setting an analyzer parallel to a polarizer.
Figure 3:
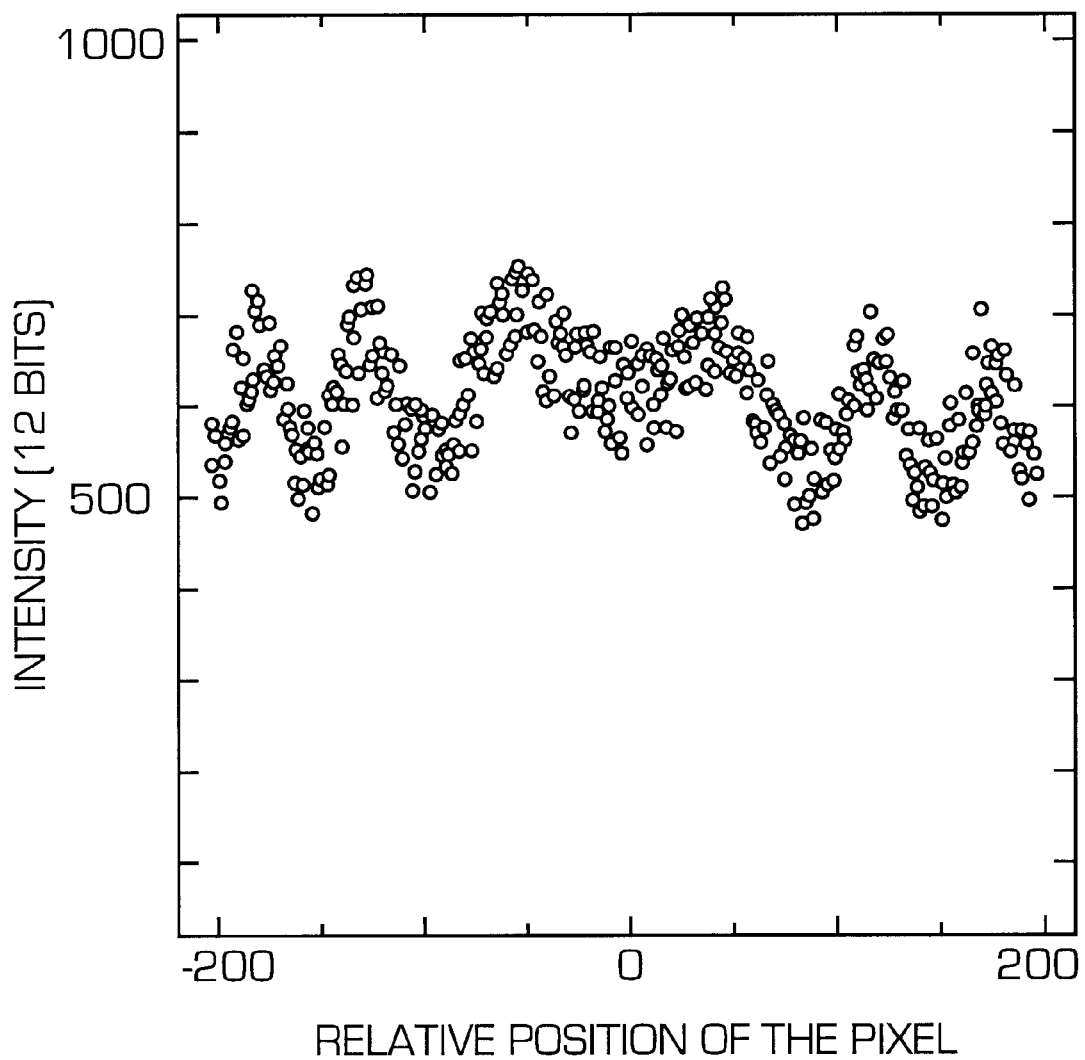
FIG. 3 is a plot showing the polarization of the liquid crystal sample A which is measured in the measuring equipment of a liquid crystal pretilt angle of FIG. 1 by setting an analyzer perpendicular to a polarizer.
Figure 4:
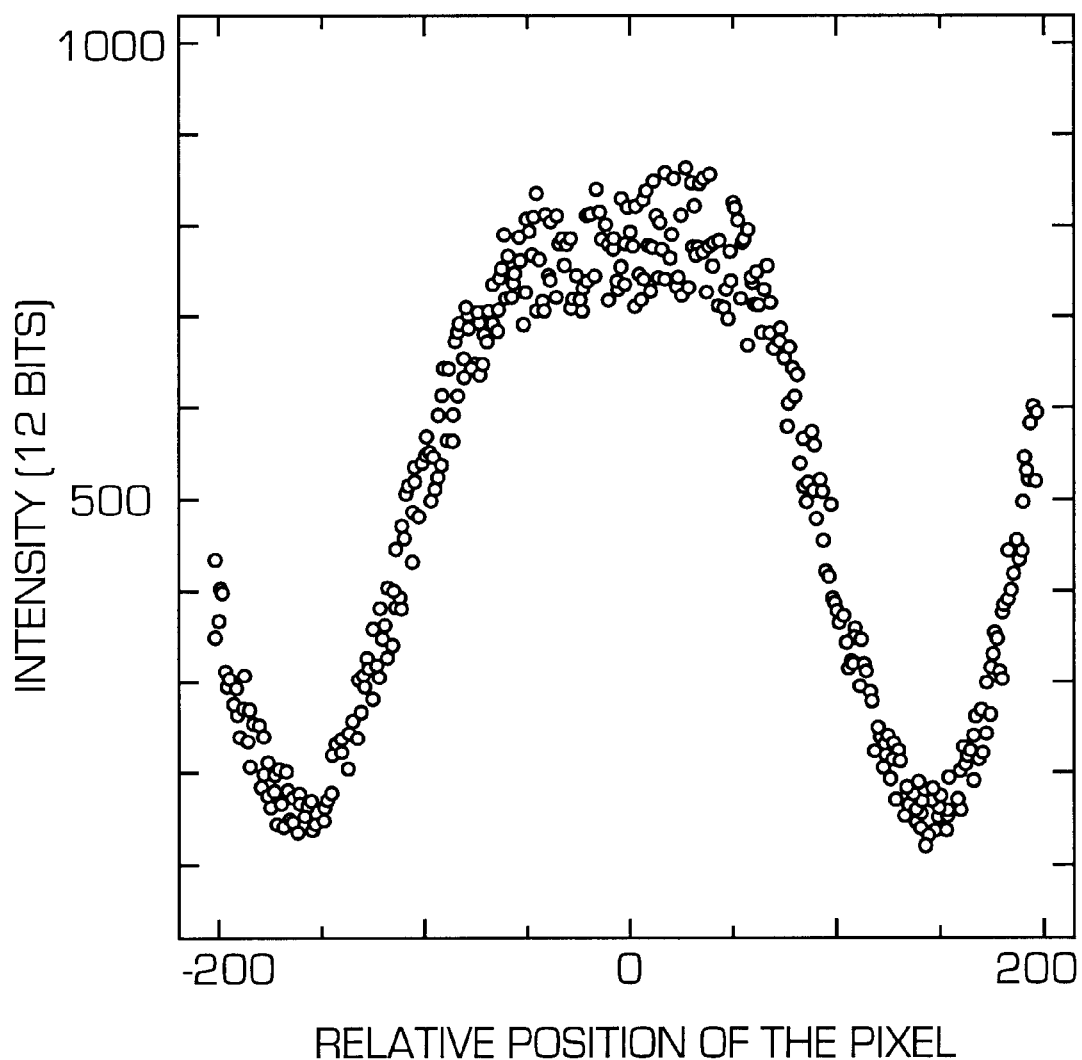
FIG. 4 is a plot showing the polarization of the liquid crystal sample B which is measured in the measuring equipment of a liquid crystal pretilt angle of FIG. 1 by setting an analyzer parallel to a polarizer.
Figure 5:
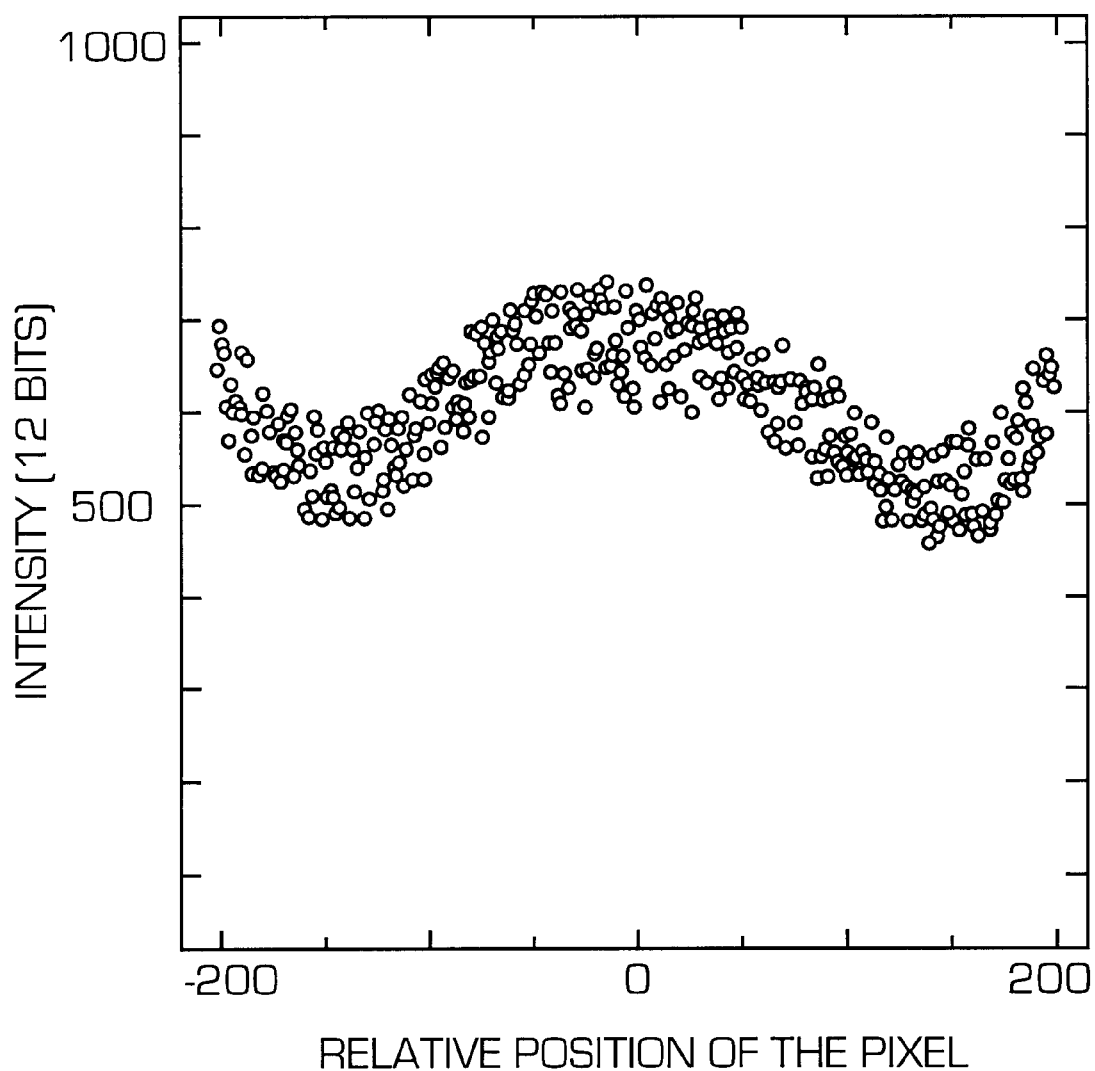
FIG. 5 is a plot showing the polarization of the liquid crystal sample B which is measured in the measuring equipment of a liquid crystal pretilt angle of FIG. 1 by setting an analyzer perpendicular to a polarizer.

A polarizer was set, by adjustment, to make a 45 degree angle between the vibration direction of the incident light and the rubbing direction of the sample. The measurements were each carried out for two azimuthal configurations of the analyzer, parallel and perpendicular to the polarizer. FIGS. 2 and 3 show, for a circular image of the sample A, the output of the pixel intensity (12 gray scales) in the direction of a diameter parallel to the polarizer, which were measured by a two-dimensional detector for parallel and perpendicular configurations of the analyzer, respectively. FIGS. 4 and 5 show, for a circular image of the sample B, the output of the pixel intensity (12 gray scales) in the direction of a diameter parallel to the polarizer, which were measured by a two-dimensional detector for parallel and perpendicular configurations of the analyzer, respectively. From these results, liquid crystal pretilt angles were obtained by a data analysis unit 50. Liquid crystal pretilt angles were estimated at 2.8 degree, 3.3 degree, 2.9 degree and 2.7 degree, respectively.

As described above, a liquid crystal pretilt angle can be obtained by measuring the incident angle dependence of the polarization of the transmitted light. Further, for the above arrangement, it is possible to use a line sensor as a detector, because pixels concerned therein are one-dimensional.

EXAMPLE 2

Figure 6:
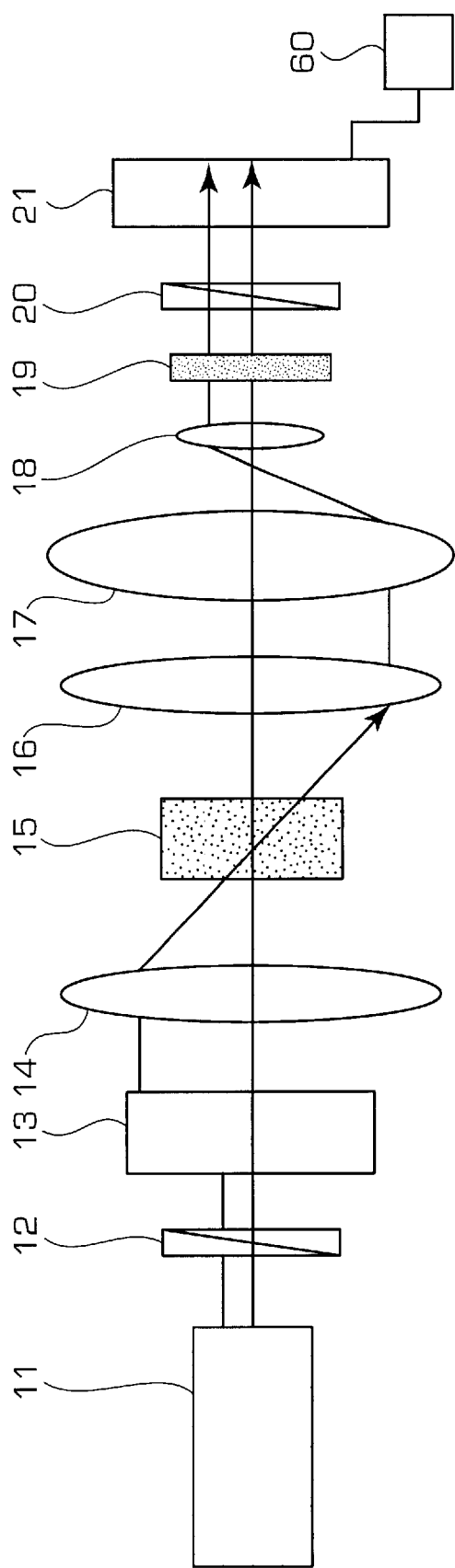
FIG. 6 is a schematic diagram illustrating another example of an equipment of measuring a liquid crystal pretilt angle in accordance with the present invention.

FIG. 6 is a schematic diagram illustrating another example of an equipment of measuring a liquid crystal pretilt angle in accordance with the present invention. Setting the linearly polarized light incident on a liquid crystal sample, a liquid crystal pretilt angle is measured through monitoring the quantity of light that is transmitting a polarizer. The light emitted from a light source 11 passes through a polarizer 12 and, being linearly polarized, is expanded by a beam expander 13. As a light source, a 1 mW He-Ne laser is used and the beam expander turns the light into a parallel beam with a diameter of approximately 25 mm. The light is then condensed by a lens 14 and set incident on a liquid crystal sample which is placed at a focal position of the lens. For this condenser, a combination lens with an aperture of 60 mm and a focal distance of 20 mm is used. The light passed through a sample 15 is returned into a parallel beam by a lens 16 having the same norm as the lens 14 and then changed into a parallel beam with a diameter of 3 mm by lenses 17 and 18. After this light passes through an analyzer 20 placed downstream of a ¼-wave plate 19, it goes into a detector 21. As a detector 21, a two-dimensional cooling-type image intensifier (512×512) manufactured by Hamamatsu Photonics is employed. This set-up is the one in which a ¼-wave plate is added, in front of the analyzer, to the arrangement of the equipment, shown in Example 1.

With this set-up, a liquid crystal sample C was measured, as described below. Glass substrates 7059 from Corning Inc. with a thickness of 1.1 mm were spin-coated with an alignment material PI-A produced by Nissan Chemical Industries Ltd.. After baked at 250° C. for 1 hour, the surface was rubbed with the rayon cloth. A cell was then assembled by sticking a pair of glass substrates together with adhesive in such a way that the rubbing directions thereof were opposite to each other. In this, the adhesive mixed with a 2 $\mu$m spacer was utilized. This cell was filled, through a capillary action, with the nematic liquid crystal produced by Merck Ltd. under the trade name of ZNI-2293.

Figure 7:
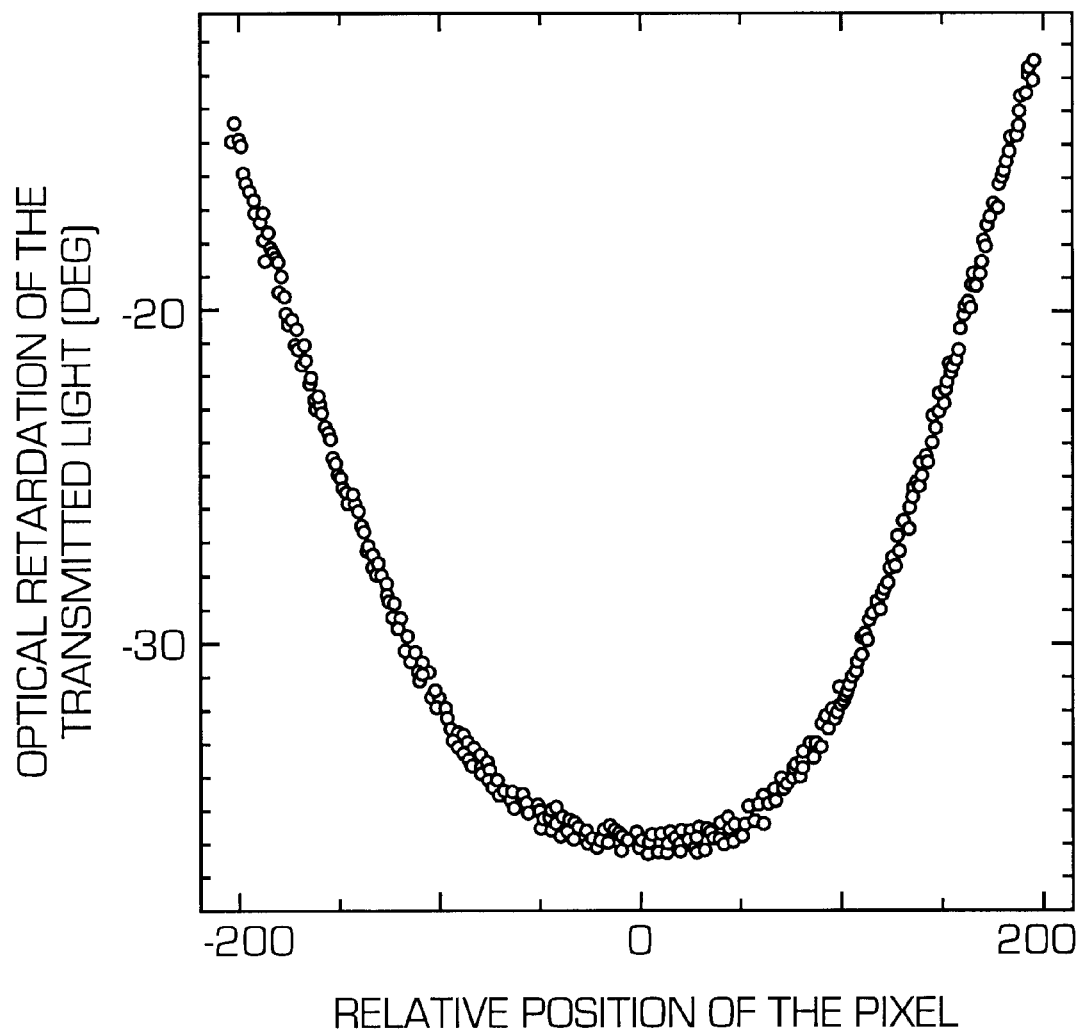
FIG. 7 is a plot showing the dependence of the optical retardation of the transmitted light on the relative position of the pixel, which is measured in the measuring equipment of a liquid crystal pretilt angle of FIG. 6.
Figure 8:
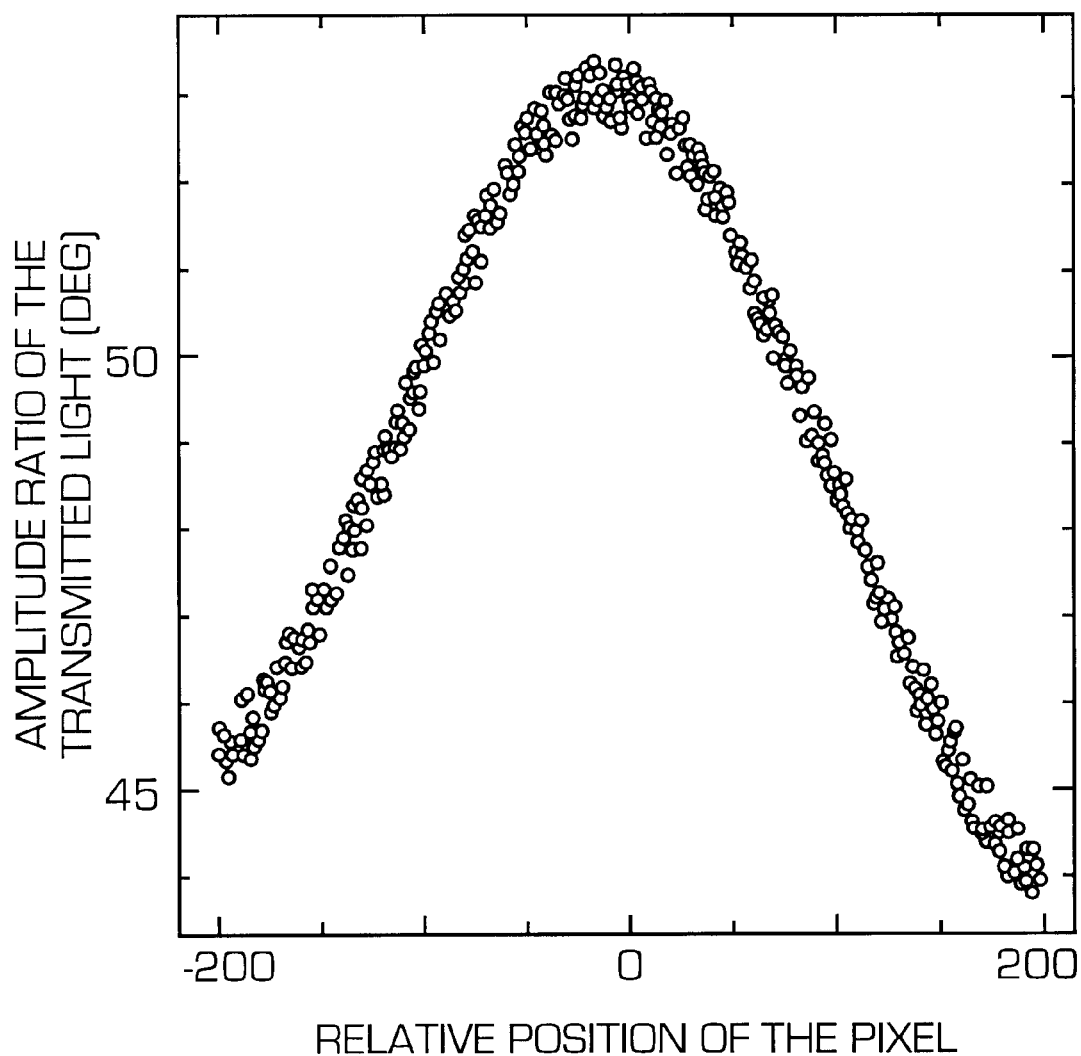
FIG. 8 is a plot showing the dependence of the amplitude ratio of the transmitted light on the relative position of the pixel, which is measured in the measuring equipment of a liquid crystal pretilt angle of FIG. 6.

A polarizer was set, by adjustment, to make a 45 degree angle between the vibration direction of the incident light and the rubbing direction of the sample. The analyzer took the parallel configuration to the polarizer, and for a circular image which was measured by a two-dimensional detector every 4 degree of the azimuth of the ¼-wave plate 19 in 90 orientations, the transmitted light intensity in pixel intensity (12 gray scales) was measured in the direction of a diameter parallel to the polarizer. From these output intensities as measured above, the polarization, namely the optical retardation and the amplitude ratio, were then obtained through Fourier synthesis over the azimuths of the wave plate. The dependences of the optical retardation as well as the amplitude ratio on the pixel position which were obtained in this way are shown in FIGS. 7 and 8. The pretilt angle was then determined, on the basis of these results, as 3.2 degree.

As described above, a liquid crystal pretilt angle can be obtained by measuring the incident angle dependence of the polarization in the transmitted light. As in Example 1, it is possible to use a one-dimensional detector as a detector in this case, as well. While the polarization measurement therein was carried out by the phaser rotation method, it is also possible to determine the polarization from the output intensity dependence by rotating the orientation of the analyzer in the set-up of FIG. 1.

EXAMPLE 3

Figure 9:
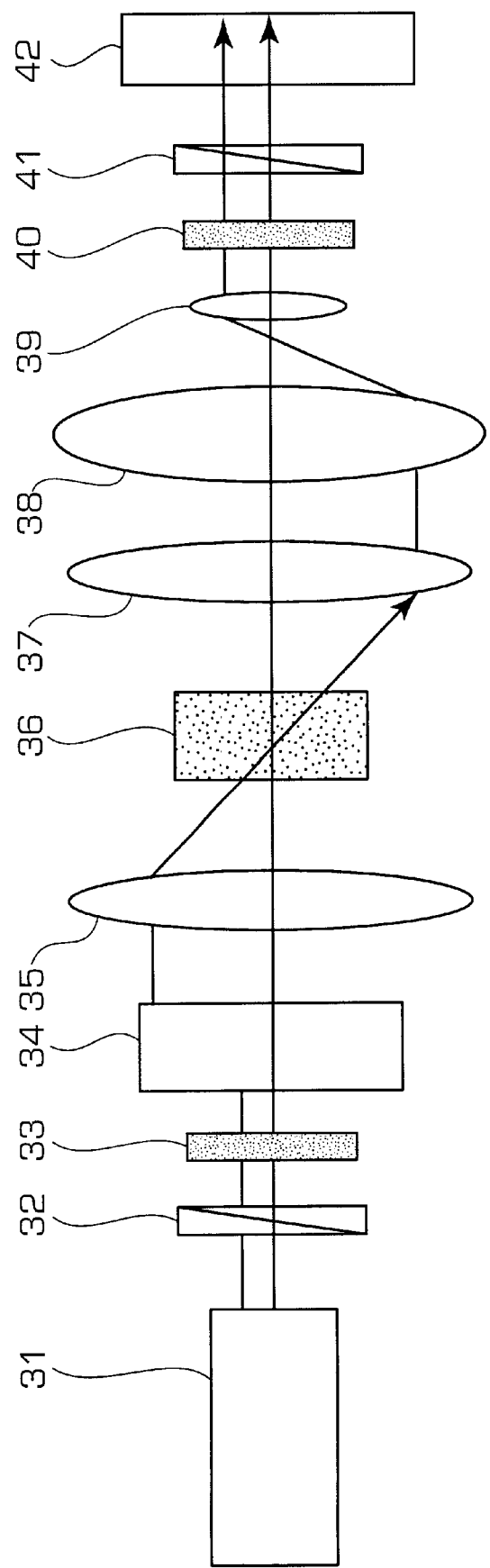
FIG. 9 is a schematic diagram illustrating another example of an equipment of measuring a liquid crystal pretilt angle in accordance with the present invention.

FIG. 9 is a schematic diagram illustrating another. example of an equipment of measuring a liquid crystal pretilt angle in accordance with the present invention. Setting the linearly polarized light incident on a liquid crystal sample, a liquid crystal pretilt angle is measured through monitoring the quantity of light that is transmitting a polarizer. The light emitted from a light source 31 passes through a polarizer 32 and a ¼-wave plate 33 and, being circularly polarized, is expanded by a beam expander 34. As a light source, a 1 mW He-Ne laser is used and the beam expander turns the light into a parallel beam with a diameter of approximately 25 mm. The light is then condensed by a lens 35 and set incident on a liquid crystal sample which is placed at a focal position of the lens. For this condenser, a combination lens with an aperture of 60 mm and a focal distance of 20 mm is used. The light passed through a sample 36 is returned into a parallel beam by a lens 37 having the same norm as the lens 35 and then changed into a parallel beam with a diameter of 3 mm by lenses 38 and 39. After this light passes through an analyzer 41 placed downstream of the ¼-wave plate 40, it goes into a detector 42. As a detector 42, a two-dimensional cooling-type image intensifier (512×512) manufactured by Hamamatsu Photonics is employed. This set-up is the one in which a ¼-wave plate is added, in front of the analyzer, to the arrangement of the equipment, shown in Example 1.

Figure 10:
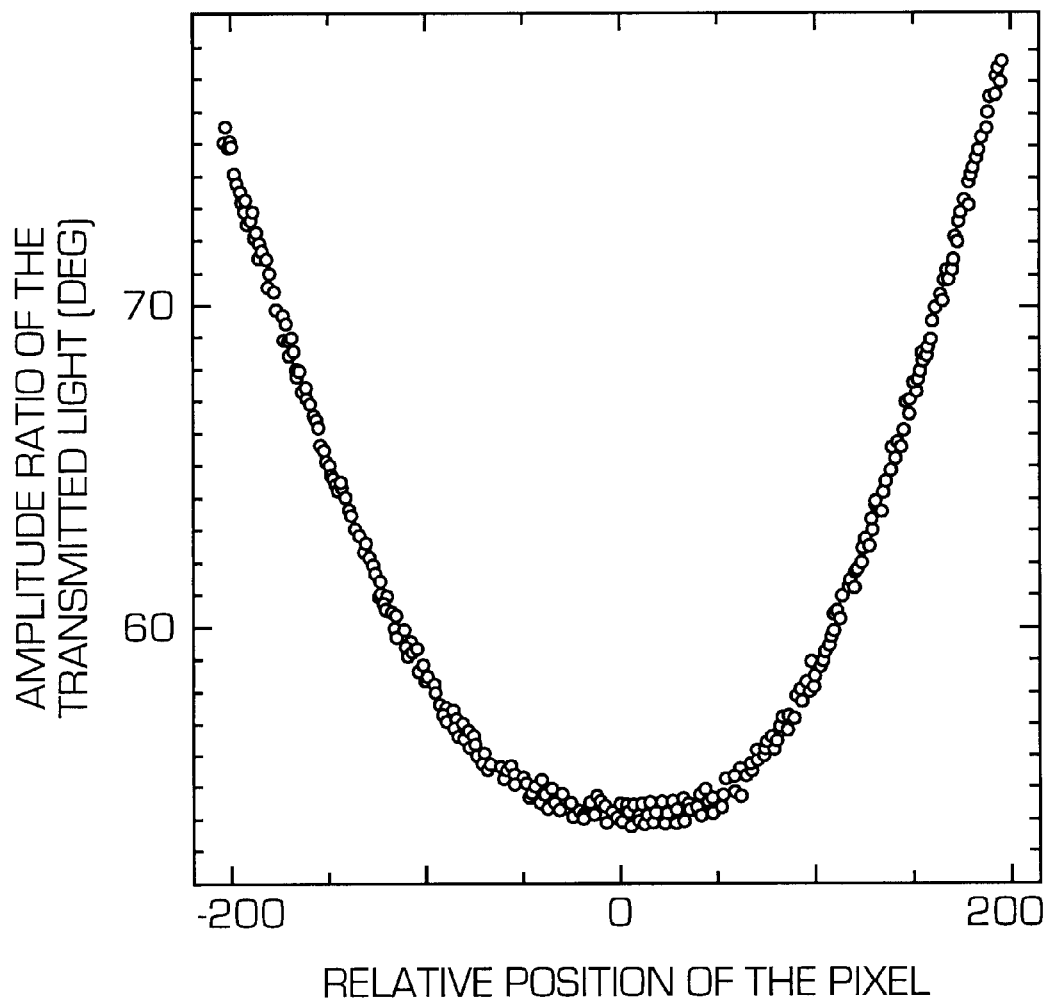
FIG. 10 is a plot showing the relationship between the amplitude ratio of the transmitted light and the relative position of the pixel.
Figure 11:
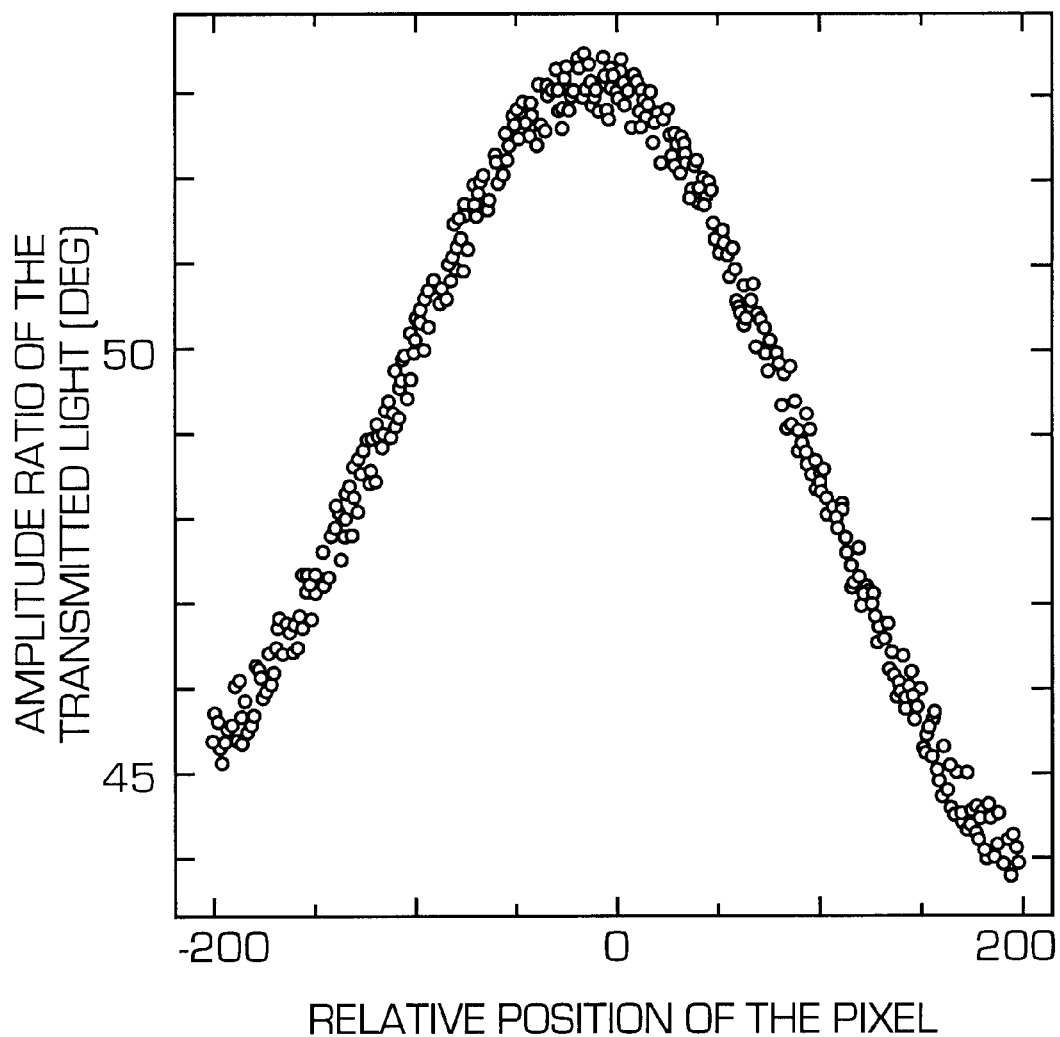
FIG. 11 is a plot showing the relationship between the amplitude ratio of the transmitted light and the relative position of the pixel.
Figure 12:
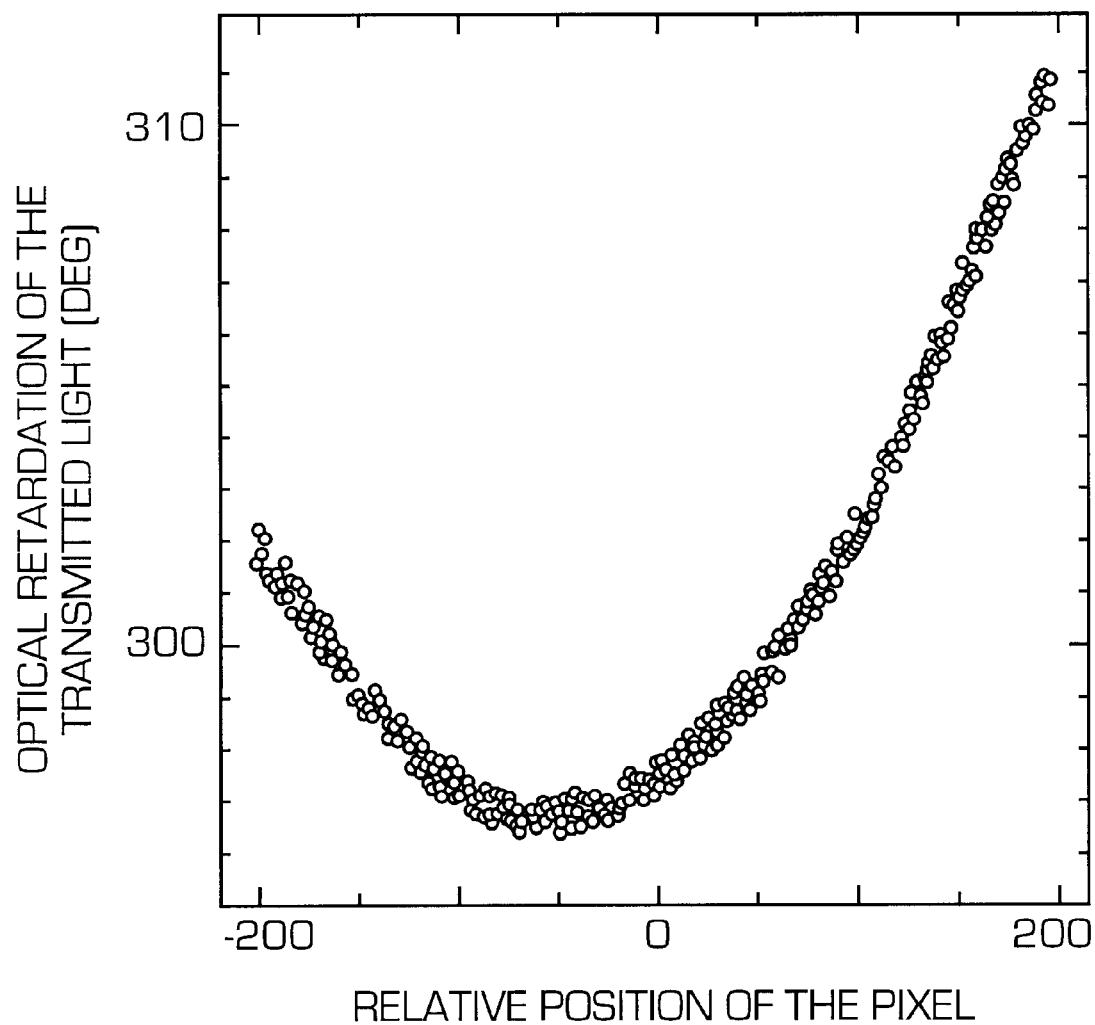
FIG. 12 is a plot showing the relationship between the optical retardation of the transmitted light and the relative position of the pixel.

With this set-up, the liquid crystal sample C which was used in Example 2 was again measured. For a circular image which was measured by a two-dimensional detector every 4 degree of the azimuth of the ¼-wave plate 40 in 90 orientations, the transmitted light intensity in pixel intensity (12 gray scales) was measured in the direction of a diameter parallel to the polarizer. From these output intensities as measured above, the polarization, namely the optical retardation and the amplitude ratio, were then obtained through Fourier synthesis over the azimuths of the wave plate. FIGS. 10 and 11 show dependences of the optical retardation and the amplitude ratio of the transmitted light on the pixel position when the incident light makes a 45 degree angle azimuthally with the rubbing direction of the sample. FIGS. 12 and 13 show dependences of the optical retardation and the amplitude ratio of the transmitted light on the pixel position when the incident light is parallel to the rubbing direction of the sample. As shown in FIGS. 11 and 13, the varied value in the amplitude ratio component of the transmitted light with the incident angle becomes the maximum when the incident light makes a 45 degree angle azimuthally with the rubbing direction of the sample. In contrast with this, the amplitude ratio component shows almost no dependency on the incident angle, when the incident light is parallel or perpendicular to the rubbing direction azimuthally. Therefore, with the circularly polarized incident light, the measurement of the polarization of the transmitted light by a two-dimensional detector can determine a liquid crystal pretilt angle by looking into the optical retardation component in an azimuthal direction where the varied value in the amplitude ratio component becomes the maximum, even for a sample with the rubbing direction unknown. While the polarization measurement therein was carried out by the phaser rotation method, it is also possible to determine the polarization from the output intensity dependence by removing the wave-plate 40 from the set-up and rotating the analyzer 41.

What is claimed is:

1. A method of measuring a liquid crystal pretilt angle comprising: transmitting an incident light with a given polarization through a non-rotating liquid crystal sample; and measuring a polarization of the light exiting said liquid crystal sample; wherein, being condensed by a lens, the transmitted light is turned to form a plurality of incident angles distributed continuously across said liquid crystal sample; and wherein, a dependence of the polarization of said transmitted light on the plurality of incident angles is measured to determine a pretilt angle of said liquid crystal sample.

2. A method of measuring a liquid crystal pretilt angle according to claim 1, wherein said incident light with a given polarization is circularly polarized light.

3. A method of measuring a liquid crystal pretilt angle according to claim 1, wherein said incident light with a given polarization is incident light with a given polarization.

4. A method of measuring a liquid crystal pretilt angle according to claim 3, wherein the polarization direction of said linearly polarized light is set to make an angle of 42 to 28 degrees to an azimuthal orientation of the liquid crystal molecules within a plane of said liquid crystal sample.

5. A method of measuring a liquid crystal pretilt angle according to claim 1, wherein said dependence of the polarization of said transmitted light is measured by a phaser rotation method, using a ¼ wave plate and an analyzer, both of which are placed downstream of said liquid crystal sample.

6. A method of measuring a liquid crystal pretilt angle comprising: transmitting an incident light with a given polarization through a stationary liquid crystal sample; and measuring a polarization of the light exiting said liquid crystal sample; wherein, said liquid crystal sample comprises a liquid crystal material, transparent substrates sandwiching said liquid crystal material and wherein, hemispherical prisms are placed on outer sides of the transparent substrates and have approximately the same refractive index as that of those transparent substrates; and by means of hemispherical prisms, said transmitted polarized light is turned to have a plurality of incident angles distributed continuously across said liquid crystal sample; and wherein, a dependence of the polarization of said transmitted light on the plurality of incident angles is measured to determine a pretilt angle of said liquid crystal sample.

7. A method of measuring a liquid crystal pretilt angle according to claim 6, wherein said incident light with a given polarization is circularly polarized light.

8. A method of measuring a liquid crystal pretilt angle according to claim 6, wherein said incident light with a given polarization is linearly polarized light.

9. A method of measuring a liquid crystal pretilt angle according to claim 8, wherein the polarization direction of said linearly polarized light is set to make an angle of 42 to 28 degrees to an azimuthal orientation of the liquid crystal molecules within a plane of said liquid crystal sample.

10. A method of measuring a liquid crystal pretilt angle according to claim 6, wherein said dependence of the polarization of said transmitted light is measured by a phaser rotation method, using a ¼-wave plate and an analyzer, both of which are placed downstream of said liquid crystal sample.

11. An apparatus for measuring a liquid crystal pretilt angle; comprising:

a light source for emitting light;

a polarizer which polarizes the emitted light from said light source;

a holder which holds a liquid crystal sample at a stationary position as an object of the measurement;

lenses placed before and behind said holder, wherein the lens placed before said holder turns the emitted light to have a plurality of incident angles continuously distributed across the liquid crystal sample held in said holder;

a means for measuring, with the light having passed through said liquid crystal sample, the amplitude ratio of said transmitted light and/or the optical retardation of said transmitted light; and a means for determining a liquid crystal pretilt angle from said measured transmitted light.

12. A method of measuring pretilt angles of liquid crystals comprising:

transmitting light having a predetermined polarization toward a stationary liquid crystal sample;

condensing said transmitted light onto a surface of said stationary liquid crystal sample to form a plurality of light rays having a plurality of incident angles with respect to said surface of said stationary liquid crystal sample;

measuring a change in polarization of each of said plurality of light rays after said plurality of light rays have passed through said stationary liquid crystal sample; and determining the pretilt angle of a liquid crystal according to the measured change in polarization of said light rays.

13. An apparatus for measuring pretilt angles of liquid crystal molecules in a liquid crystal sample, said apparatus comprising:

a light source for emitting light;

a polarizer for polarizing light emitted from said light source;

a condensing lens for bending light polarized by said polarizer into a plurality of rays;

a holder to hold said liquid crystal sample in a fixed position such that said plurality of rays from said condensing lens form a plurality of respective incident angles on a surface of said liquid crystal sample; and an optical detection system to measure light passing through said liquid crystal sample, such that a change in polarization is measured for each of said plurality of rays according to their respective incident angles; and means for determining a pretilt angle of a liquid crystal according to light measured by said optical detection system.

* * * * *